(12) United States Patent
Hacini-Rachinel et al.

(10) Patent No.: US 10,398,720 B2
(45) Date of Patent: Sep. 3, 2019

(54) COMPOUND OF THE AVERMECTIN FAMILY OR OF THE MILBEMYCIN FAMILY FOR THE TREATMENT AND/OR PREVENTION OF ATOPIC DERMATITIS

(71) Applicant: GALDERMA SA, Cham (CH)

(72) Inventors: Feriel Hacini-Rachinel, Biot (FR); Emmanuel Vial, Nice (FR); André Jomard, Saint Vallier de Thiey (FR)

(73) Assignee: GALDERMA SA, Cham (CH)

( * ) Notice: Subject to any disclaimer, the term of this patent is extended or adjusted under 35 U.S.C. 154(b) by 0 days.

(21) Appl. No.: 15/648,055

(22) Filed: Jul. 12, 2017

(65) Prior Publication Data

US 2017/0304340 A1 Oct. 26, 2017

Related U.S. Application Data

(63) Continuation of application No. 15/100,302, filed as application No. PCT/EP2014/075927 on Nov. 28, 2014, now abandoned.

(30) Foreign Application Priority Data

Nov. 29, 2013 (EP) ..................................... 13306633

(51) Int. Cl.
*A61K 31/7048* (2006.01)
*A61K 9/00* (2006.01)
*A61K 47/10* (2017.01)
*A61K 9/06* (2006.01)
*A61K 31/365* (2006.01)
*A61K 47/02* (2006.01)
*A61K 47/12* (2006.01)
*A61K 47/14* (2017.01)
*A61K 47/18* (2017.01)
*A61K 47/26* (2006.01)
*A61K 47/32* (2006.01)
*A61K 47/34* (2017.01)

(52) U.S. Cl.
CPC ........ *A61K 31/7048* (2013.01); *A61K 9/0014* (2013.01); *A61K 9/06* (2013.01); *A61K 31/365* (2013.01); *A61K 47/02* (2013.01); *A61K 47/10* (2013.01); *A61K 47/12* (2013.01); *A61K 47/14* (2013.01); *A61K 47/183* (2013.01); *A61K 47/26* (2013.01); *A61K 47/32* (2013.01); *A61K 47/34* (2013.01)

(58) Field of Classification Search
CPC .................................................. A61K 31/7048
See application file for complete search history.

(56) References Cited

U.S. PATENT DOCUMENTS

| | | | |
|---|---|---|---|
| 8,491,928 B2 | 7/2013 | Mallard et al. | |
| 8,598,129 B2 | 12/2013 | Manetta et al. | |
| 8,815,816 B2 | 8/2014 | Manetta et al. | |
| 8,897,218 B2 | 11/2014 | Mathison et al. | |
| 9,089,587 B2 | 7/2015 | Jacovella et al. | |
| 9,125,927 B2 | 9/2015 | Kaoukhov et al. | |
| 9,233,117 B2 | 1/2016 | Jacovella et al. | |
| 9,233,118 B2 | 1/2016 | Jacovella et al. | |
| 9,457,038 B2 | 10/2016 | Kaoukhov et al. | |
| 2007/0116731 A1 | 5/2007 | Astruc et al. | |
| 2009/0264517 A1 | 10/2009 | Kaoukhov et al. | |
| 2012/0004200 A1 | 1/2012 | Nadau-Fourcade et al. | |
| 2012/0035123 A1 | 2/2012 | Jomard et al. | |
| 2015/0190416 A1 | 7/2015 | Kabashima et al. | |

FOREIGN PATENT DOCUMENTS

| | | |
|---|---|---|
| WO | 03032976 A1 | 4/2003 |
| WO | 2004093886 A1 | 11/2004 |
| WO | 2014017319 A1 | 1/2014 |

OTHER PUBLICATIONS

Morita et al. Journal of Dermatological Science, 1999, vol. 19, pp. 37-43 (Year: 1999).*
Saeki et al., "Guidelines for Management of Atopic Dermatitis", Journal of Dermatology, 2009, p. 563-577, vol. 36, Japanese Dermatological Association.
International Search Report corresponding to PCT/EP2014/075927, dated Mar. 3, 2015.

\* cited by examiner

*Primary Examiner* — James D. Anderson
(74) *Attorney, Agent, or Firm* — Sunit Talapatra; Foley & Lardner LLP (57) ABSTRACT

A method of treating and/or preventing atopic dermatitis is described. The method includes use of a compound of the avermectin family, possibly ivermectin, or a compound of the milbemycin family in a pharmaceutically acceptable carrier.

11 Claims, 6 Drawing Sheets

COMPOUND OF THE AVERMECTIN FAMILY OR OF THE MILBEMYCIN FAMILY FOR THE TREATMENT AND/OR PREVENTION OF ATOPIC DERMATITIS

This application is a continuation of U.S. patent application Ser. No. 15/100,302, filed May 28, 2016, which is a National Stage of PCT/EP2014/075927, filed Nov. 28, 2014, and designating the United States (published Jun. 4, 2015, as WO 2015/079016 A1), which claims priority under 35 U.S.C. § 119 to EP 13306633.2, filed Nov. 29, 2013, each hereby expressly incorporated by reference in its entirety and each assigned to the assignee hereof.

The present invention relates to pharmaceutical compositions which are suitable for the treatment and/or prevention of atopic dermatitis.

Dermatitis derives from Greek language with "derma" meaning skin and "itis" meaning inflammation. Thus, dermatitis corresponds to skin inflammation that is classified in several specific and distinct types of dermatitis according to the localization, causes and symptoms thereof. Non exhaustive examples of dermatitis are contact dermatitis, herpetiformis dermatitis, acrodermatitis, exfoliative dermatitis, perioral dermatitis, seborrheic dermatitis and atopic dermatitis.

Atopic dermatitis is a condition of the epidermis which affects a large number of individuals genetically predisposed to atopy, including infants, children and pregnant women. In general, atopic dermatitis starts in infancy and in early childhood, particularly around two months of age. Approximately, 50% of atopic dermatitis starts before two years of age. It is very rare that atopic dermatitis develops its first symptom in adulthood.

Atopic dermatitis is an increasingly common pruritic inflammatory skin disorder due to complex interactions between the genetic predispositions and environmental factors. Atopic dermatitis has a complex etiology that involves abnormal immunological and inflammatory pathways that include defective skin barrier, exposure to environmental agents and neuropsychological factors. The diagnosis of atopic dermatitis is based on clinical presentation of skin erythematous plaques, eruption, and/or lichenification, typically in flexural areas accompanied by intense pruritus and cutaneous hypersensitivity. Pathological examination reveals spongiosis, hyperkeratosis and parakeratosis in acute lesions and marked epidermal hyperplasia, acanthosis, and perivascular accumulation of lymphocytes and mast cells (mastocytes) in chronic lesions.

Although the exact pathophysiology of atopic dermatitis has not yet been clearly understood, it has been reported that atopic dermatitis has at least two major components corresponding to a damaged skin barrier and a deregulated immune response.

Indeed, it has been reported that extrinsic atopic dermatitis is developed by the IgE related immunomechanism and it has been confirmed that the increase of IgE is related to the dysfunction of cell mediated immunity in atopic dermatitis patients.

It has also been noted that dryness of the skin is one of the predominant factors in the generation of atopic dermatitis, notably due to a reduced expression of filaggrin in the skin of individuals affected by atopic dermatitis as demonstrated by Seguchi et al. (Arch. Dermatol. Res., 1996, 288, 442-446) and by Jensen et al. (J. Invest. Dermatol., 2004, 122, 1423-1431). Bieber et al. (N. Eng. J. Med. 2008, 358, 1483-94) have even demonstrated that atopic dermatitis was only damaged skin barrier related in 70% of the patients and that filaggrin mutation was involved in 30% of the patients.

Considering the known causes, mechanisms and symptoms of atopic dermatitis up to date, therapeutic agents for the treatment and the prevention of atopic dermatitis have been developed.

Several authors have proposed pharmaceutical or dermatological compositions in order to treat symptoms of atopic dermatitis such as dry skin, erythematous plaques, eruption, lichenification, intense pruritus or cutaneous hypersensitivity and, to a greater extent, to compensate for the epithelial barrier deficiency. For example, pyrrolidone carboxylic acid (Takaoka, JP2004168763) and citrulline or certain amino acids such as glycine, methionine and alanine (Harano et al., WO2005077349) have been used as a moisturizing gent in emollient compositions for treating atopic dermatitis. Tezuka (JP08020525) have proposed shampoos containing a complex of sodium montmorillonite with a moisturizing agent, which itself can be urea, amino acids, proteins, proteins, pyrrolidone carboxylic acid or a silk protein hydrolysate.

Natural or synthetic immune inhibitors, anti-histamine agents, and steroids have also been used in pharmaceutical compositions in order to treat dermatitis atopic by reducing IgE production with the aim to reduce the immune response. For example, cyclosporin A holds the limelight as immune inhibitors or calcineurin inhibitor and is marked by Novartis under the name Sandimmun®. However, the conventional treating agents for atopic dermatitis using steroid and anti-histamine agents can only temporarily relieve symptoms. In addition, when topical or oral steroids are administered for a long term, the skin of a patient wears thin and osteoporosis is induced. Tacrolimus, which is marked under the names Prograf®, Advagraf® and Protopic®, may also be cited for treating atopic dermatitis as a calcineurin inhibitor leader. However, this drug is suspected of carrying a cancer risk and FDA (Food Drug Administration) has even issued a health warning in March 2005.

According to the complexity of the pathophysiology of atopic dermatitis and the side effects of the current treatments of this inflammatory skin disease, there is a need for developing new pharmaceutical compositions and use thereof for treating and/or preventing atopic dermatitis.

In this context, the inventors have surprisingly demonstrated that a pharmaceutical composition comprising a compound of the avermectin family or of the milbemycin family, particularly ivermectin, even at low dose, can be effectively used in the treatment and/or prevention of atopic dermatitis with less or no side effect.

The present invention relates to a pharmaceutical composition comprising a compound of the avermectin family or of the milbemycin family in a pharmaceutically acceptable carrier, for use in the treatment and/or prevention of atopic dermatitis.

In a particular embodiment, the compound of the avermectin family is chosen from the group consisting of ivermectin, avermectin, abamectin, doramectin, eprinomectin and selamectin, aversectin B, AB or C, emamectin B1a, emamectin B1b and their derivatives. More preferably, the compound of the avermectin family is ivermectin.

In another particular embodiment, the compound of the milbemycin family is chosen from the group consisting of lepimectin, milbemectin, milbemycin oxime and moxidectin, 6'-ethyllepimectin, 6'-methyllepimectin and its derivatives or nemadectin $\alpha$, $\beta$, $\gamma$ or $\delta$.

Advantageously, the pharmaceutical composition according to the invention is used for the treatment and/or prevention of atopic dermatitis in pregnant women, children and infants, more advantageously in infants.

The composition for use in the context of the invention is administered by topical application, preferably in the form of an emulsion, a cream, a lotion type, a gel or a solution.

According to the invention, the composition comprises from 0.001 to 5%, by weight of a compound of the avermectin family or of the milbemycin family, preferably of ivermectin relative to the total weight of the composition, preferably from 0.001 to 1%, more preferably from 0.001 to 0.3%, and even more preferably from 0.001 to 0.05%.

In a preferred embodiment, the composition comprises in water:
Ivermectin 1.0
Glycerol 4.0
Acrylate C10-30 alkyl acrylate crosspolymer 0.2
Methyl para-hydroxybenzoate 0.2
Disodium EDTA 0.05
Citric acid monohydrate 0.05
Isopropyl palmitate 4.0
Cetyl alcohol 3.5
Stearyl alcohol 2.5
Oleyl alcohol 2.0
Ceteareth-20 3.0
Sorbitan monostearate 2.0
Dimethicone 200 20 cs 0.5
Propyl para-hydroxybenzoate 0.1
Propylene glycol 2.0
Phenoxyethanol 1.0
10% sodium hydroxide qs pH
as % by weight relative to the total weight of the composition.

The inventors have surprisingly identified that ivermectin presents a therapeutic interest for treating and/or preventing atopic dermatitis. In particular, inventors have shown the therapeutic efficiency of topically applied ivermectin with an admitted mouse model of atopic dermatitis.

Accordingly, the present invention relates to a pharmaceutical composition comprising a compound of the avermectin family or of the milbemycin family in a pharmaceutically acceptable carrier, for use in the treatment and/or prevention of atopic dermatitis.

The present invention also relates to a method for treating and/or preventing atopic dermatitis comprising administering to a subject suffering of atopic dermatitis an effective amount of a composition comprising a compound of the avermectin family or of the milbemycin family in a pharmaceutically carrier.

The present invention further relates to a method for treating and/or preventing atopic dermatitis comprising administering to a subject suffering of atopic dermatitis a composition comprising a compound of the avermectin family or of the milbemycin family in a pharmaceutically carrier, thereby reducing total IgE production, cytokine production, and/or eosinophils and mastocytes number.

The present invention also concerns the use of a pharmaceutical composition comprising a compound of the avermectin family or of the milbemycin family in a pharmaceutically acceptable carrier for the preparation of a drug for treating and/or preventing atopic dermatitis.

In a particular embodiment, the compound of the avermectin family is chosen from the group consisting of ivermectin, avermectin, abamectin, doramectin, eprinomectin and selamectin, aversectin B, AB or C, emamectin B1a, emamectin B1b and their derivatives.

More preferably, the compound of the avermectin family is ivermectin.

In another particular embodiment, the compound of the milbemycin family is chosen from the group consisting of lepimectin, milbemectin, milbemycin oxime and moxidectin, 6'-ethyllepimectin, 6'-methyllepimectin and its derivatives or nemadectin $\alpha$, $\beta$, $\gamma$ or $\delta$.

The preferred subjects concerned by the methods to treat and/or prevent atopic dermatitis are pregnant women, children and infants, advantageously infants.

Ivermectin is a mixture of two compounds belonging to the avermectin class, 5-O-demethyl-22,23-dihydroavermectin $A_{1a}$ and 5-O-demethyl-22,23-dihydroavermectin $A_{1b}$. They are also known as 22,23-dihydroavermectin $B_{1a}$ and 22,23-dihydroavermectin $B_{1b}$. Ivermectin contains at least 80% of 22,23-dihydroavermectin $B_{1a}$ and less than 20% of 22,23-dihydroavermectin $B_{1b}$. This active agent is part of the avermectin class, a group of macrocyclic lactones produced by the bacterium *Streptomyces avermitilis*.

In the middle of the 1980s, ivermectin was presented as a broad-spectrum antiparasitic medicinal product for veterinary use (Campbell et al.: Science, 1983, 221, 823-828). Ivermectin is effective against most common intestinal worms, except tapeworms, most acarids and some lice. In particular, it exhibits considerable affinity for the glutamate-dependent chloride channels present in invertebrate nerve cells and muscle cells. Its binding to these channels promotes an increase in membrane permeability to chloride ions, resulting in hyperpolarization of the nerve or muscle cell. Neuromuscular paralysis which can lead to the death of certain parasites results therefrom. Ivermectin also interacts with other ligand-dependant chloride channels, such as those involving the neuromediator GABA (gamma-aminobutyric acid).

Ivermectin is more particularly disclosed as an anthelmintic used in humans for the treatment of river blindness caused by *Onchocerca volvulus*, of gastrointestinal strongyloidiasis (anguillulosis) (product Stromectol®), and of human scabies (Meinking et al., N. Engl. J. Med., 1995, 333, 26-30)) and also for the treatment of microfilaraemai diagnosed or suspected in individuals suffering from lymphatic filariasis due to *Wuchereria bancrofti*.

Manetta and Watkins (WO 2004/093886) have suggested the use of ivermectin for producing a topical pharmaceutical composition for the treatment of rosacea and other dermatologic conditions.

However, ivermectin has never been disclosed or suggested in compositions for the treatment of atopic dermatosis.

The present invention therefore relates to a pharmaceutical composition comprising a compound of the avermectin family or of the milbemycin family in a pharmaceutically acceptable carrier, for use in the treatment and/or prevention of atopic dermatitis.

According to the invention, the pharmaceutical composition is formulated in a pharmaceutically acceptable carrier meaning that the pharmaceutical composition comprises ivermectin in association with a pharmaceutically acceptable carrier. The carrier must be "acceptable" in the sense of being compatible with the other ingredients of the formulations and not deleterious to the recipient thereof. Particularly, in the context of the invention, the carrier is compatible with human skin.

The pharmaceutical composition is advantageously administered by topical application and, therefore, is in a form suitable for topical application to the skin. For example, it may be in the form of an optionally gelled, oily solution, an optionally two-phase dispersion of the lotion type, an emulsion obtained by dispersion of a fatty phase in an aqueous phase (O/W) or vice versa (W/O), or a triple emulsion (W/O/W or O/W/O) or a vesicular dispersion of ionic and/or non-ionic type. This topical composition may be in anhydrous form, in aqueous form or in the form of an emulsion. These compositions are prepared according to the usual methods. According to this invention, a composition in the form of an emulsion obtained by dispersion of a fatty phase in an aqueous phase (O/W) is preferably used.

This composition may be more or less fluid and may be in the form of salves, emulsions, creams, milks, ointments, impregnated pads, syndets, solutions, gels, sprays or aerosols, foams, suspensions, lotions or sticks. Preferably, the composition used in the present invention is in the form of an emulsion, of a cream, of a lotion type, of a gel, or of a solution, and more preferably in the form of an emulsion.

The composition of the invention is preferably formulated according to the formulations disclosed in the patent application WO 2004/093886. Some formulations are presented at example 1.

In the context of the present invention, the pharmaceutical composition comprising a compound of the avermectin family or of the milbemycin family is used in the treatment and/or prevention of atopic dermatitis, preferably in pregnant women, newborn baby, infants and children and, more preferably, in infants.

Indeed, as shown in the examples of the present application, ivermectin shows efficiency agonist atopic dermatitis, even at very low dose and with less or no side effect.

As used herein, a newborn baby is a baby from 0 to 28 days, an infant is a baby from 1 month to 2 years and a child is aged from 2 years to 14 years or from 2 years to the age of puberty.

The composition of the invention comprises from 0.001 to 5%, by weight of a compound of the avermectin family or of the milbemycin family relative to the total weight of the composition. Preferably, the composition comprises from 0.001 to 1% by weight of a compound of the avermectin family or of the milbemycin family relative to the total weight of the composition. Advantageously, the composition comprises from 0.001 to 0.3%, advantageously from 0.001 to 0.05% by weight of a compound of the avermectin family or of the milbemycin family relative to the total weight of the composition. Again more advantageously, the composition comprises a total amount of a compound of the avermectin family or of the milbemycin family suitable for its administration in particular individuals such as pregnant women, newborn baby, infants and children. The compound of the avermectin family is preferably ivermectin.

Following examples illustrate further aspect and advantages of the invention which are no way limiting in nature.

EXAMPLES

Example 1: Compositions of the Invention

Example 1a: Composition 1

| Ingredients | % by weight relative to the total weight of the composition |
| --- | --- |
| Ivermectin | 1.00 |
| Glycerol | 4.0 |
| Aluminium magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 2.5 |
| Steareth-20 | 3.0 |
| Sorbitan stearate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 1b: Composition 2

| Ingredients | % by weight relative to the total weight of the composition |
| --- | --- |
| Ivermectin | 1.00 |
| Glycerol | 4.0 |
| Steareth-2 | 1.0 |
| Steareth-21 | 2.0 |
| Aluminium magnesium silicate/titanium dioxide/silica | 1.0 |
| Methyl para-hydroxybenzoate | 0.2 |
| Propyl para-hydroxybenzoate | 0.1 |
| Disodium EDTA | 0.05 |
| Citric acid monohydrate | 0.05 |
| Isopropyl palmitate | 4.0 |
| Glyceryl/PEG 100 stearate | 2.0 |
| Self-emulsifiable wax | 1.0 |
| Palmitostearic acid | 2.00 |
| Dimethicone 20-350 cS | 0.5 |
| Propylene glycol | 4.0 |
| Glyceryl triacetate | 1.00 |
| Phenoxyethanol | 0.5 |
| 10% sodium hydroxide | qs pH |
| Water | qs 100 |

Example 1c: Composition 3

| Ingredients | % by weight relative to the total weight of the composition |
|---|---|
| Ivermectin | 1.00 |
| Glycerol | 4.0 |
| Acrylate C10-30 alkyl acrylate crosspolymer | 0.15 |
| Methyl para-hydroxybenzoate | 0.2 |
| Disodium EDTA | 0.05 |
| Citric acid monohydrate | 0.05 |
| Isopropyl myristate | 4.0 |
| Cetyl alcohol | 3.0 |
| Stearyl alcohol | 2.0 |
| Self-emulsifiable wax | 0.8 |
| Palmitostearic acid | 0.5 |
| Steareth-20 | 2.0 |
| Sorbitan palmitate | 1.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 1d: Composition 4

| Ingredients | % by weight relative to the total weight of the composition |
|---|---|
| Ivermectin | 1.00 |
| Glycerol | 4.0 |
| Aluminium magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 3.0 |
| Steareth-20 | 3.0 |
| Sorbitan palmitate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 1e: Composition 5

| Ingredients | % by weight relative to the total weight of the composition |
|---|---|
| Ivermectin | 1.00 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 1f: Composition 6

| Ingredients | % by weight relative to the total weight of the composition |
|---|---|
| Ivermectin | 1.4 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 2: Evaluation by the Topical Route of the Immunomodulatory Potential of Ivermectin in the *Dermatophagoides*-Induced Atopic Dermatitis (AD)-Like Mouse Model

1. Material and Methods 1.1. Der f-Induced AD Mouse Model

The *Dermatophagoides farinae* (Der f)-induced AD mouse model has been shown to be suitable for the study of the atopic dermatitis pathophysiology and the evaluation of new therapies (J. Invest. Dermatol., 2009, 129, 31-40).

Der f has been purchased from Greer Laboratories and a Der f solution has been prepared at 12.5 mg/ml in 70% DMSO in MilliQ water.

1.2. Compounds 1.2.1. Ivermectin

Ivermectin has been delivered by Galderma and 0.003, 0.01, 0.03, and 0.1% ivermectin solutions in acetone have been performed.

1.2.2. Triamcinolone Acetonide and Tacrolimus

Triamcinolone acetonide and tacrolimus have been chosen as positive control for the Der f model. 0.05% triamcinolone acetonide and 0.1% tacrolimus solutions in acetone have been performed.

1.3. Mice

Balb/c mice strain has been used for the study. These animals have been obtained from controlled breeding and were specific pathogen free. The animals have been provided by Janvier SAS, France.

1.4. Protocol

AD-like lesions have been induced once a week by topical application of 20 μl of Der f solution on the right ear for 5 weeks at day 1, day 8, day 22, day 29 and day 36. Mice have been daily treated from day 19 to day 36 with the different solutions administrated by the topical route.

Measurement of ear thickness have been monitored before and 24 hours after each allergen application. After day 19, ears have been daily measured before compound application.

Blood samples have been collected into appropriate vials under isoflurane anaesthesia for further analysis (IgE). Mice have been then immediately euthanized.

After mouse euthanasia, the right ear has been collected and has been washed in ethanol 70% and has been rinsed in PBS. Three skin biopsies have then been collected for cytokines profiles, eosinophil peroxidase (EPO) quantification and histological slides in order to quantify the mastocytes and in order to measure the epidermis thickness.

2. Results

—Der f/Acetone Group

Figure 1:
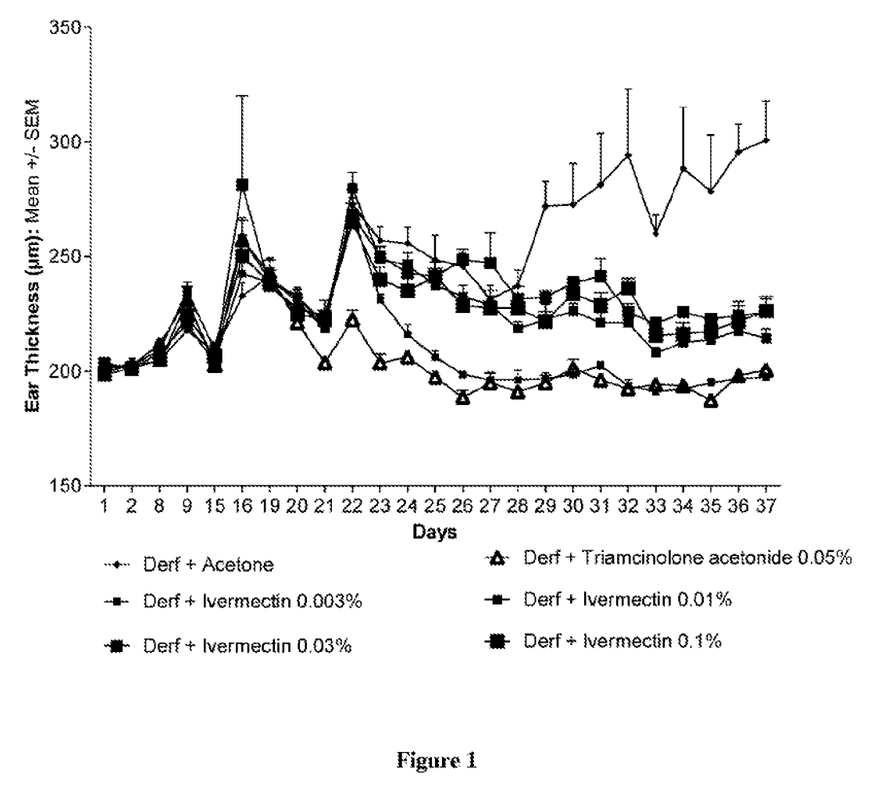
FIG. 1: Measurement of the average mouse ear thickness after Der f-induced cutaneous inflammation and topically application of 0.003, 0.01, 0.03 and 0.1% ivermectin, and 0.05% triamcinolone acetonide.
Figure 3:
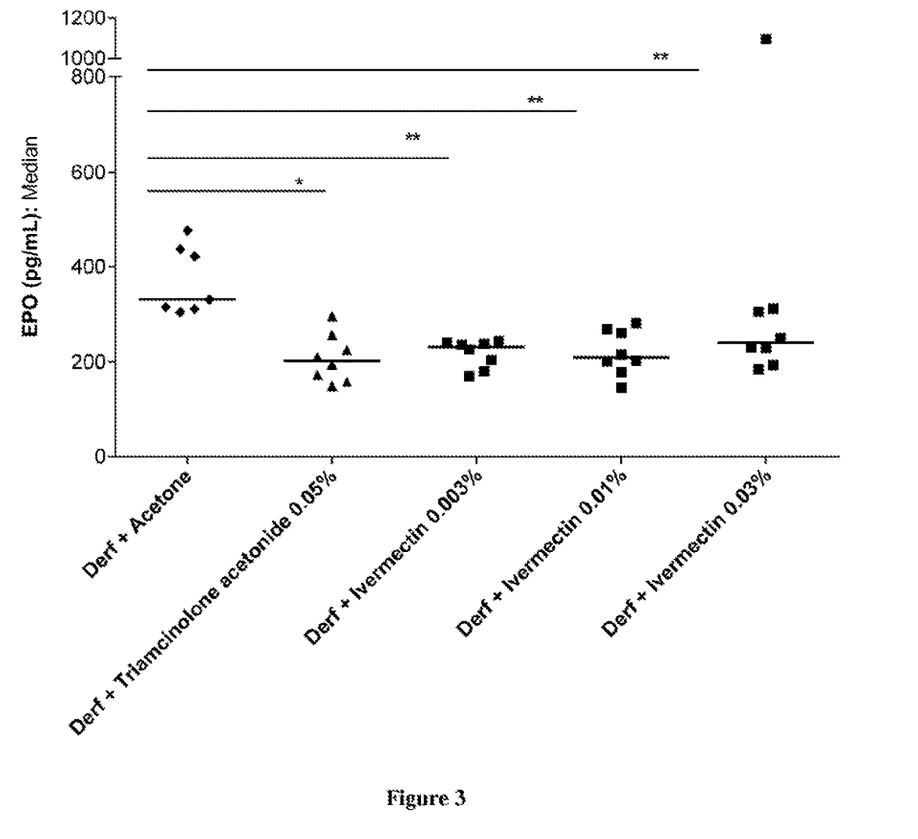
FIG. 3: Eosinophil peroxidase (EPO) quantification after Der f-induced cutaneous inflammation and topically application of 0.003, 0.01, and 0.03% ivermectin, and 0.05% triamcinolone acetonide.
Figure 4:
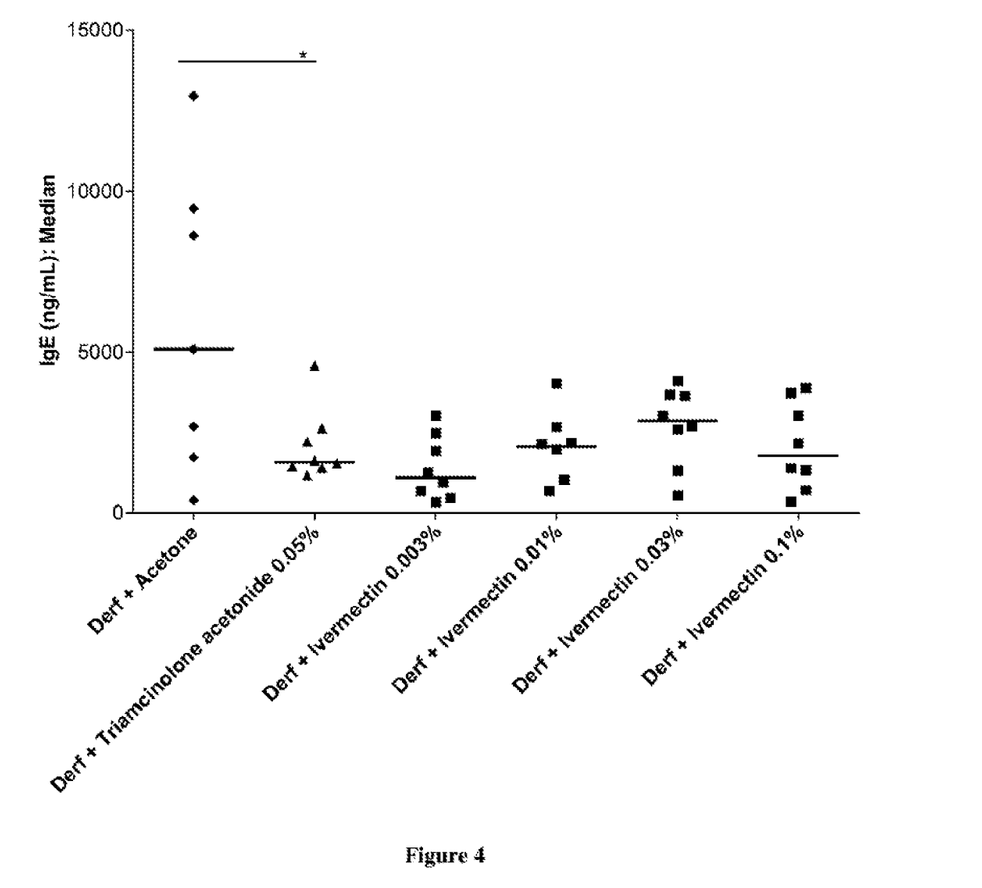
FIG. 4: IgE quantification after Der f-induced cutaneous inflammation and topically application of 0.003, 0.01, 0.03, and 0.1% ivermectin, and 0.05% triamcinolone acetonide.
Figure 5:
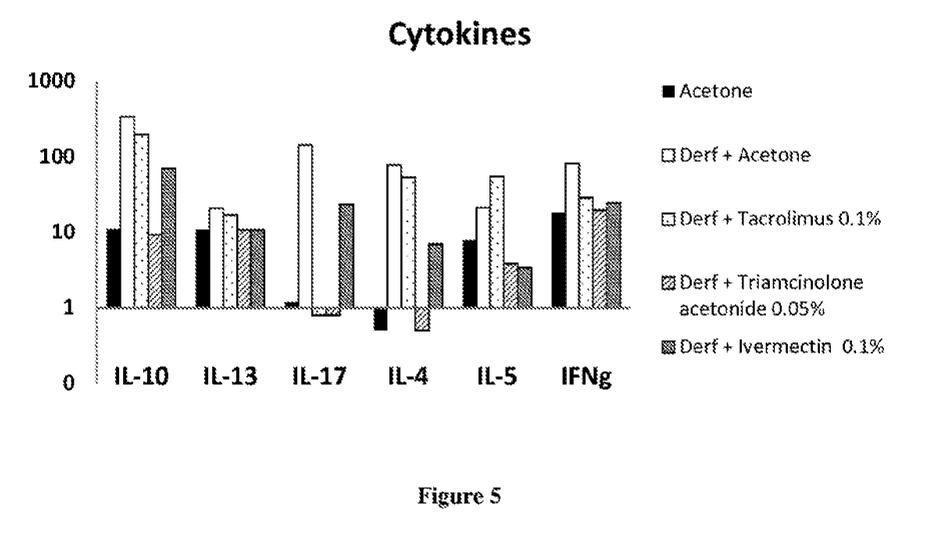
FIG. 5: Interleukin quantification (IL-10, IL-13, IL-17, IL-4, IL-5 and IFNg) after Der f-induced cutaneous inflammation and topically application of 0.1% ivermectin, 0.05% triamcinolone acetonide, and 0.1% tacrolimus.
Figure 6:
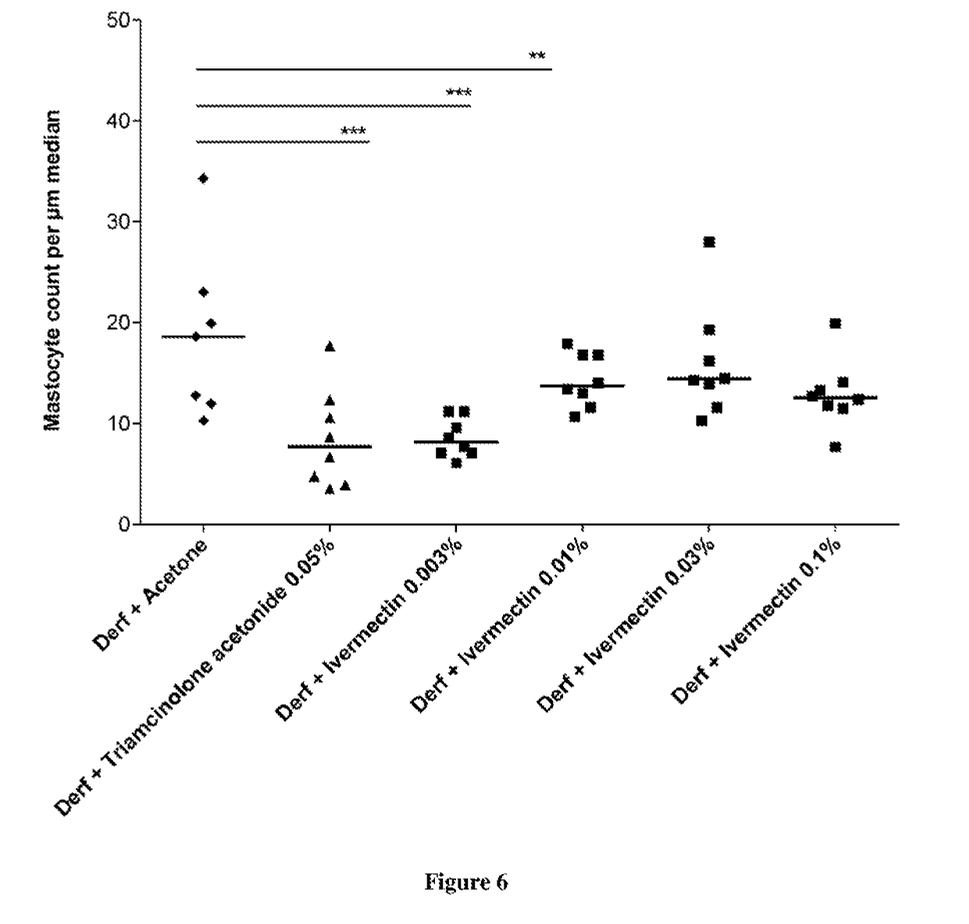
FIG. 6: Mastocytes count after Der f-induced cutaneous inflammation and topically application of 0.003, 0.01, 0.03, and 0.1% ivermectin, and 0.05% triamcinolone acetonide.

The once weekly application of Der f induces a significant increase in ear thickness (FIG. 1), in EPO (FIG. 3) representing an enhanced eosinophils infiltration, in total seric IgE (FIG. 4), and in cytokine concentration (FIG. 5). It also induced epidermal hyperplasia with a marked mastocytes infiltration (FIG. 6). These observations are representative of a Th2 response.

—Der f/Positive Controls

Figure 2:
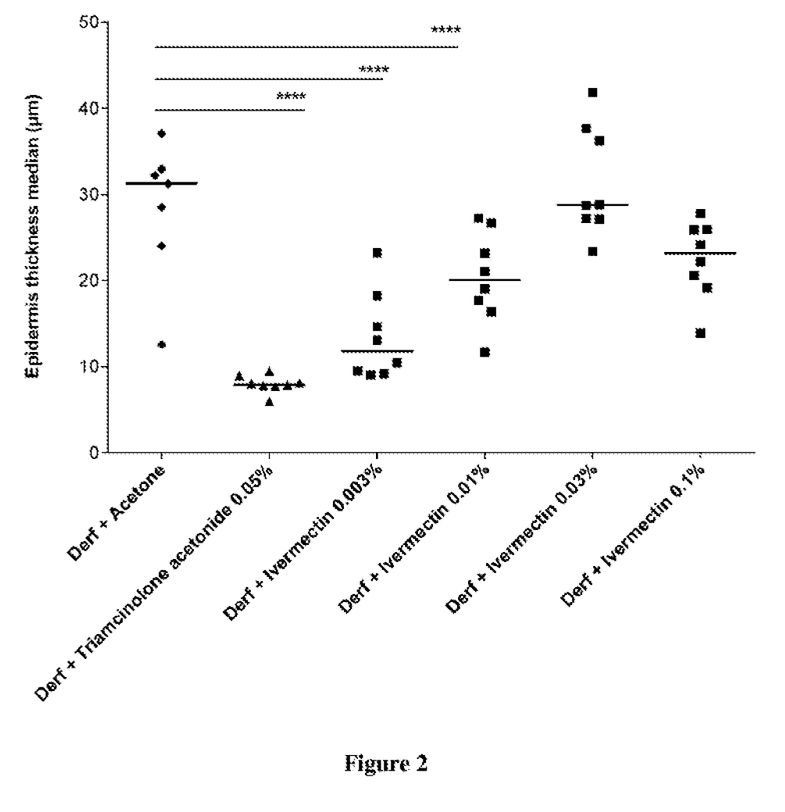
FIG. 2: Measurement of the mouse epidermis thickness median after Der f-induced cutaneous inflammation and topically application of 0.003, 0.01, 0.03, and 0.1% ivermectin, 0.05% triamcinolone acetonide.

As expected, triamcinolone acetonide and tacrolimus completely inhibit the inflammatory response. Indeed triamcinolone acetonide totally reduces ear edema (FIG. 1), EPO (FIG. 3), IgE secretion (FIG. 4) and cytokine concentration (FIG. 5). It also strongly reduces the epidermal thickness (FIG. 2) and the mastocyte count (FIG. 6). In addition, tacrolimus totally reduces ear edema (FIG. 1) and cytokine concentration, particularly, interleukin IL-17 production (FIG. 5).

—Der f/Ivermectin

As observed, Ivermectin is surprisingly able to reduce the inflammatory response induced by Der f application. Indeed, it significantly decreases ear edema (FIG. 1), EPO (FIG. 3), IgE secretion (FIG. 4) and cytokine production (FIG. 5). It also lessens the epidermal thickness (FIG. 2) and the mastocyte count within the dermis (FIG. 6). As important to note that ivermectin at 0.003% is able to reduce the inflammatory response to the same extent as triamcinolone acetonide at 0.05% and as tacrolimus at 0.1%. The higher concentrations of ivermectin (0.01, 0.03, and 0.1%) even though showing a marked anti-inflammatory response, remain less potent than the weakest concentration (0.003%).

3. Conclusion

These data clearly demonstrate that topical treatment with ivermectin can reduce the skin inflammation and confirm the great interest of ivermectin for treating and/or preventing atopic dermatitis. In addition, inventors have surprisingly demonstrated an inverse dose response with the inflammatory activity. The use of ivermectin is well therefore suitable for treating and/or preventing atopic dermatitis in particular individuals such as pregnant women, children and infants.

The invention claimed is:

1. A method for treating atopic dermatitis, the method comprising: topically applying to the skin of a human subject in need thereof a pharmaceutical composition comprising 0.003% ivermectin by weight, relative to the total weight of the composition.

2. The method as defined by claim 1, wherein the human subject in need thereof is a pregnant woman, a child, or an infant.

3. The method as defined by claim 1, wherein the pharmaceutical composition is in the form of an emulsion, a cream, a lotion, a gel, or a solution.

4. The method as defined by claim 2, wherein the human subject in need thereof is a pregnant woman.

5. The method as defined by claim 2, wherein the human subject in need thereof is a child.

6. The method as defined by claim 2, wherein the human subject in need thereof is an infant.

7. The method as defined by claim 3, wherein the pharmaceutical composition is in the form of an emulsion.

8. The method as defined by claim 3, wherein the pharmaceutical composition is in the form of a cream.

9. The method as defined by claim 3, wherein the pharmaceutical composition is in the form of a lotion.

10. The method as defined by claim 3, wherein the pharmaceutical composition is in the form of a gel.

11. The method as defined by claim 3, wherein the pharmaceutical composition is in the form of a solution.

* * * * *